United States Patent [19]

Walt

[11] Patent Number: 5,252,494
[45] Date of Patent: Oct. 12, 1993

[54] FIBER OPTIC SENSORS, APPARATUS, AND DETECTION METHODS USING CONTROLLED RELEASE POLYMERS AND REAGENT FORMULATIONS HELD WITHIN A POLYMERIC REACTION MATRIX

[75] Inventor: David R. Walt, Lexington, Mass.

[73] Assignee: Trustees of Tufts College, Medford, Mass.

[21] Appl. No.: 859,869

[22] Filed: Mar. 30, 1992

Related U.S. Application Data

[63] Continuation-in-part of Ser. No. 409,462, Sep. 19, 1989, Pat. No. 5,114,864, which is a continuation-in-part of Ser. No. 294,175, Jan. 6, 1989, abandoned, which is a continuation-in-part of Ser. No. 878,128, Jun. 25, 1986, Pat. No. 4,822,746, and Ser. No. 305,176, Feb. 2, 1989, Pat. No. 5,143,853, which is a continuation of Ser. No. 878,128, Jun. 25, 1986, Pat. No. 4,822,746.

[51] Int. Cl.$^5$ ............... G01N 33/544; G01N 33/545; G01N 33/549
[52] U.S. Cl. ..................... 436/528; 385/123; 385/125; 385/144; 385/145; 422/58; 422/82.05; 422/82.06; 422/82.07; 422/82.08; 422/82.09; 422/82.11; 435/7.7; 435/7.72; 435/7.9; 435/288; 435/291; 435/808; 436/164; 436/172; 436/531; 436/535; 436/800; 436/805; 436/807
[58] Field of Search ............ 422/58, 82.05, 82.06, 422/82.07, 82.08, 82.09, 82.11; 435/808, 7.7, 7.72, 7.9, 288, 291; 436/164, 528, 531, 535, 805, 800, 807, 172; 385/123, 125, 144, 145; 356/73.1

[56] References Cited

U.S. PATENT DOCUMENTS

| | | | |
|---|---|---|---|
| 4,387,164 | 6/1983 | Hevey et al. | 422/56 |
| 4,577,109 | 3/1986 | Hirschfeld | 422/82.07 |
| 4,849,172 | 7/1989 | Yafuso et al. | 422/82.08 |
| 4,919,891 | 4/1990 | Yafuso et al. | 422/82.08 |
| 4,925,268 | 5/1990 | Iyer et al. | 422/82.07 |
| 4,954,318 | 9/1990 | Yafuso et al. | 422/82.08 |
| 4,999,306 | 3/1991 | Yafuso et al. | 422/82.07 |
| 5,006,314 | 4/1991 | Gourley et al. | 422/82.07 |
| 5,028,395 | 7/1991 | Sebille et al. | 422/82.07 |
| 5,098,659 | 3/1992 | Yim et al. | 422/82.07 |

OTHER PUBLICATIONS

Langer, R., *Science* 249: 1527-1533 (1990).
Siegel, R. A. and R. Langer, *Pharm. Res.*:2-10 (1984).
Paul, D. R. and F. W. Harris, ACS Symposium Series, vol. 33, 1976, pp. 1-14.

*Primary Examiner*—David Saunders
*Assistant Examiner*—Christopher L. Chin
*Attorney, Agent, or Firm*—David Prashker

[57] ABSTRACT

An improved fiber optic sensor, sensing apparatus, and methods for making optical detections are provided. The fiber optic sensor employs a fiber optic strand to convey light energy, an immobilized polymeric reaction matrix, and at least one controlled release polymeric carrier within said reaction matrix comprising a controlled release polymer material and a releasable reagent formulation able to react with the analyte of interest. The optic sensors and sensor construction have been demonstrated to be both functionally useful and long serving in duration.

13 Claims, 3 Drawing Sheets

FIBER OPTIC SENSORS, APPARATUS, AND DETECTION METHODS USING CONTROLLED RELEASE POLYMERS AND REAGENT FORMULATIONS HELD WITHIN A POLYMERIC REACTION MATRIX

CROSS-REFERENCES

This application is a Continuation-In-Part of application Ser. No. 409,462 filed Sep. 19, 1989, now U.S. Pat. No. 5,114,864 which is a Continuation-In-Part of application Ser. No. 294,175 filed Jan. 6, 1989, now abandoned; which is a Continuation-in-Part of application Ser. No. 878,128 filed Jun. 25, 1986 now U.S. Pat. No. 4,822,746 and also of application Ser. No. 305,176 filed Feb. 2, 1989, now U.S. Pat. No. 5,143,853 which is a Continuation of application Ser. No. 878,128 filed Jun. 25, 1986, now U.S. Pat. No. 4,822,746.

RESEARCH SUPPORT

The research for the present invention was supported by a grant from the Environmental Protection Agency through the Tufts Center for Environmental Management.

FIELD OF THE INVENTION

The present invention is concerned with optical sensors and optical sensing apparatus utilizing colorimetric or fluorometric techniques as qualitative and quantitative detection systems; and is particularly directed to fiber optic sensors utilizing continuous release delivery systems capable of delivering sensing ligands and reagents into polymeric reaction matrices for optical determinations.

BACKGROUND OF THE INVENTION

The science and instrumentation of spectroscopy as developed over the last century has become increasingly expanded and specialized as the various methods and applications of analysis came into existence. Today, spectroscopy has been divided into individual and distinctly different methods and instrumentation systems for: ultraviolet and visible spectrophotometry; fluorescence and phosphorescence spectrophotometry; flame emission and atomic absorption spectrometry; atomic emission spectroscopy; infrared spectrophotometry; raman spectroscopy; nuclear magnetic resonance spectroscopy; electron spin resonance spectroscopy; and refractometry and interferometry. Of these, the optical sensors and optical sensing detection systems utilizing the ultraviolet and visible absorption methods and the fluorescence and phosphorescence excitation and emission systems are perhaps the best known and commonly utilized.

The essentials of an ultraviolet/visible spectrometry instrumentation system utilizes the principles of absorption photometry; and comprises in its simplest forms a light energy source, focusing optics, and unknown or standard sample cuvette, a wavelength isolation device, and a detector with amplifier and readout system. From an engineering standpoint, it is desirable that this type of absorption photometry system be detector limited; that is, the limiting factor should be the noise generated by the detector. Anything that can be done to increase signal levels at the detector is therefore desirable. The measure of performance is usually defined as precision, or photometric accuracy. In terms of construction, one recognizes the differences between single-beam and double-beam light paths; and whether the photometer module is a direct reading or employs a balance circuit. Other available instrumentation features include double monochromatic and dual wavelength systems.

In comparison, fluorescence and phosphorescence is a physical phenomenon based upon the ability of some molecules to absorb and emit light. With these molecules, the absorption of light energy (photons) at specified wavelengths is followed by the emission of light from the molecule of a longer wavelength and at a lower energy state. Such emissions are called fluorescence if the emission is relatively long-lived, typically a rate of from $10^{-9}$ to $10^{-7}$ seconds. Phosphorescence lifetimes usually fall within the range from $10^{-4}$ to 10 seconds. The most striking difference between the two forms are the conditions under which each type of photoluminescence is observed. Fluorescence is usually seen at moderate temperature in the liquid solution. Phosphorescence is seen in rigid media, usually at very low temperatures.

A simple generalized instrument suitable for fluorescence and phosphorescence spectrophotometry usually comprises: a source of light energy; a primary filter or excitation monochromator; a sample cell; a secondary filter or emission monochromator; a photodetector; and a data readout device. In contrast to ultraviolet/visible instrumentation, two optical systems are necessary. The primary filter or excitation monochromator selects specific bands or wavelengths of radiation from the light source and directs them through the sample in the sample cell. The resultant emission or luminescence is isolated by the secondary filter or emission monochromator and directed to the photodetector which measures the intensity of the emitted radiation. For observance of phosphorescence, a repetitive shutter mechanism is required.

For more complete and detailed information, the following publications and references are provided, the text of which are expressly incorporated by reference herein: Willard, Merritt, Dean, and Settle, *Instrumentation Methods of Analysis*, 6th edition, Wadsworth Publishing Company, Belmont, California, 1981; Joseph R. Kakowicz, *Principles Of Fluorescence Spectroscopy*, Plenum Press, New York, 1983; Skog and West, *Fundamentals Of Analytical Chemistry*, 4th edition, Saunders College Publishing, 1982.

A more recent event has been the development of fiber optic sensors and instrumentation systems utilizing ultraviolet, visible, and/or fluorometric photometry techniques. Such fiber optic sensors and sensing apparatus are fast becoming established analytical tools for remote and in-situ optical sensing determinations. The development of fiber optic sensors and their applications are illustrated by the following publications Angel, S. M., *Spectroscopy* 2:38–48 (1987); Hilliard, L. A., *Analytical Proceedings* 22:210–224 (1985); Boisde et al., *Talanta* 35:75–82(1988); Wolfbeis, O. S., *Pure and Appl. Chem.* 59:663–672 (1987); Seitz, W. R., *Anal. Chem.* 56:16A–34A (1984); and Seitz, W. r., *CRC Critical Reviews In analytical Chemistry* 19:135–173 (1988).

Regardless of which light energy system and photometric basis is employed, an ideal optical sensotr must have the ability to measure the concentration of an analyte continuously over the entire range of changes in the optical properties of the sensing reagent. To date, this sensor ability has ben based on the availability of suitable, long-lasting, reversible chemistries and reagants. The systems are thus based and dependent upon the ability of the reagent to first associate and then disassociate reversibly with the specific analyte—a requirement which has eliminated many colorimetric and fluorometric compositions and reactive ligands from being used in such sensors because these compositions are irreversible in their reactions. Accordingly, because many ultraviolet, visible, and fluorescent compositions form a tightly binding complex with the analyte of interest or utilize reagents which generate an irreversibly colored or fluorescent aduct product for reaction with the analyte of interest, these compositions and photometric techniques have been generally avoided and deemed inappropriate for use with fiber optic sensors. In those limited numbers of optic sensors utilizing irreversible chemistries, these may be employed if they operate in an integrating mode; however, they must be replenished frequently with fresh sensing reagent ligands because of the irreversible nature of their reaction with the analyte to be detected.

Clearly, therefore, a fiber optic sensor which releases irreversible reagents and ligands reactive with an analyte of interest and which does not require frequent replenishment of reagents and provides accurate and reliable modes of delivery would be recognized and appreciated by ordinary practitioners within this art as a major improvement and substantive advance in this field.

SUMMARY OF THE INVENTION

The present invention provides a fiber optic sensor for optical detections of a plurality of testing fluids believed to contain an analyte of interest, said fiber optic sensor comprising:

an optical fiber strand able to convey light energy of a determinable wavelength, said optical fiber strand having a proximal end, a distal end, and a strand length;

a porous polymeric reaction matrix immobilized substantially at the distal end of said optical fiber strand, each analyte of interest to be detected being able to permeate said polymeric reaction matrix; and at least one controlled release polymer carrier within said immobilized porous polymeric reaction matrix, each said controlled release polymer carrier comprising at least one controlled release polymer and at least one releasable reagent formulation, each analyte of interest permeating said polymeric reaction matrix reacting with such reagent formulation as has been controllably released into said polymeric reaction matrix.

Other aspects of the present invention provide a fiber optic sensing apparatus for making optical determinations; and methods for making optical determinations using the fiber optic sensor and the fiber optic sensing apparatus.

DETAILED DESCRIPTION OF THE FIGURES

The present invention may be more easily and completely understood when taken in conjunction with the accompanying drawing, in which.

DETAILED DESCRIPTION OF THE PREFERRED EMBODIMENTS

The present invention is an improvement in fiber optic sensor design and instrumentation systems which utilize a polymeric matrix as a receiving and reaction vehicle for the controlled and sustained release and delivery of reagent formulations from polymer carriers. These reagent formulations, after release, are able to react reversibly or irreversibly with a specific molecule or analyte of interest from a plurality of different fluids or samples seriatim within the polymeric reaction matrix. The improved fiber optic sensor is expected and intended to be used broadly in many different fields including: spectrometry utilizing ultraviolet, visible, and near infrared absorption photometry or using fluorescent and phosphorescent emission systems; chemical and biochemical analyses for medical, environmental, and biological applications; and process control systems for manufacturing and quality assurance in industry. All the presently known colorimetric or fluorometric phenomena, mechanisms of action, techniques, and applications can be employed directly with the various embodiments of the present invention.

All embodiments of the present invention encompass fiber optic chemicals sensors which are based upon and utilize releasable reagent ligands or formulations which have been initially trapped and immobilized within a continuous release polymer as a plurality of discrete carriers; and all of these discrete polymer carriers are themselves held and contained within a single polymeric reaction matrix. This technique for preparing and immobilizing the encompassing and encapsulating polymeric reaction matrix is simple, straightforward, and reliable; and it overcomes the major limitation of using only reversible reagents and indicating systems when constructing fiber optic sensors.

I. A pH Sensing Embodiment

Figures 1, 2:
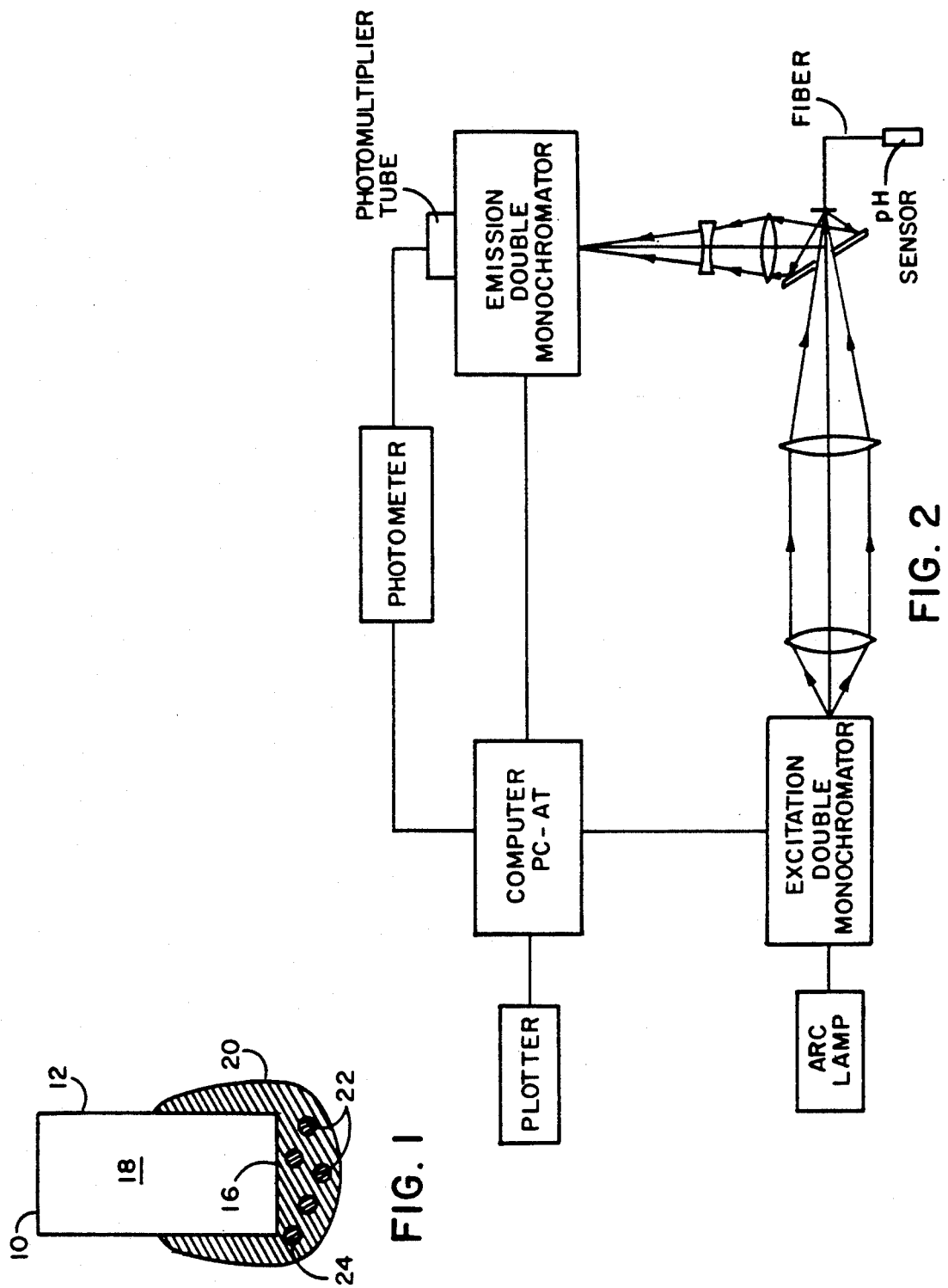
FIG. 1 is a cross-sectional view of a first embodiment of the fiber optic sensor.
FIG. 2 is a block diagram of a fiber optic sensor apparatus useful for making optical determinations.

One highly useful embodiment of the improved fiber optic sensor is illustrated by FIG. 1. This embodiment is constructed as a long-lasting pH fiber optic sensor providing a controlled and sustained release of a pH-sensitive fluorescent dye, hydroxypyrene trisulfonic acid or "HPT", upon contact with a test fluid. The fluorescent dye, HPTS, has been first incorporated into ethylene-vinyl acetate (hereinafter "EVA") copolymer particles; and, after polymerization into discrete polymer carrier form, has been immobilized within a surrounding polymeric reaction matrix. The HPTS in each discrete polymer carrier is released slowly and continuously from the EVA carrier into the surrounding polymeric reaction matrix upon contact with any aqueous fluid. No tangible housing or separate reaction chamber as such is thus required for the sensor construction or operation. The specific embodiment of FIG. 1 is disclosed in complete detail and empirically evaluated in the experiments described hereinafter. However, the construction of this first embodiment sensor will effectively serve to describe the essential components generally as required for all embodiments of the present invention regardless of specific characteristics, capabilities, uses, or applications.

The improved construction and design of the fiber optic of FIG. 1 employs multiple polymer carriers, each of which comprises at least one controlled release polymer (such as EVA particulates and spheres) and at least one reagent formulation (such as a fluorophore). These discrete polymer carriers collectively and cumulatively serve as a plurality of dispersed continuous release delivery vessels. Moreover, these multiple polymer carriers containing a releasable reagent formulation are held and contained within a discrete, porous, and preferably fluid permeable, polymeric reaction matrix, which is itself immobilized and positioned at and around the distal end of an optical fiber strand. By this organization and mode of construction, when each of the test fluids being individually evaluated is placed in fluid contact with the immobilized polymeric reaction matrix of the sensor, both the analyte of interest and the test fluid will penetrate and diffuse through the immobilized porous and fluid-permeable polymeric reaction matrix; and thus concomitantly make fluid reactive contact with the plurality of continuous release polymer carriers—whereby the fluid erodible polymer carrier releases the reagent formulation in a controlled and sustained manner into the substance of the polymeric reaction matrix for reaction with such analyte of interest as has permeated the polymeric reaction matrix. The immobilized porous polymeric reaction matrix thus serves as a discrete reaction chamber as well as a capsular housing which allows both the test fluid and the analyte of interest to diffuse and flow through the midst of the polymeric reaction matrix material. The only meaningful limitations to this mode of interaction are the pore size and porosity of the matrix material; and the need for the analyte of interest to react with the released reagent formulation to form a reaction adduct in sufficient quantities to be detected optically.

Thus, not only does the porous polymeric reaction matrix bring the various reactants into direct and intimate reactive contact; but the polymeric reaction matrix also provides the fixed location and physical site where the reaction product(s) are formed and where the reaction product(s) are held for the time duration when spectral measurements and optical determinations are made via the optical fiber strand.

As seen in FIG. 1, the essential construction and design of the improved fiber optic sensor 10 comprises an optical fiber strand 12 having a proximal end 14 (not shown), a distal end 16, and a strand length or body 18. Immobilized substantially at and around the distal end 16 is a discrete polymeric reaction matrix 20 which is porous and permeable (in varying degree) to each test fluid and each analyte of interest being optically evaluated. While the true size, dimensions, volume, and configuration of the polymeric reaction matrix 20 may vary greatly, in every embodiment of the present sensor, the polymeric reaction matrix will comprise and contain at least one and preferably a plurality of fluid erodible polymer carriers 22. Each polymer carrier 22 is comprised of a continuous release polymer material such as ethyl vinyl acetate copolymer; and includes at least one sustained release reagent formulation 24 such as a fluorophoric or chromophoric dye reagent. Typically, the polymer carriers 22 take form as preformed particles, spheres, or other discrete vessels held within the substance of the polymeric reaction matrix 20; and are continuously eroded by each of the test fluids seriatim as the permeate and diffuse through the thickness of the porous polymeric reaction matrix 20. In this manner, the dye reagent formulations initially held within the polymer carriers become eroded and continuously released from each of the polymer carriers via the fluids passing into and through the polymeric reaction matrix; and, once released into the thickness or substance of the polymeric reaction matrix, these dye reagent formulations react with such analyte of interest as is also then present within the polymeric reaction matrix.

In actual use, the sensor construction illustrated by FIG. 1 is employed with a test fluid or liquid containing at least one specific molecule or analyte of interest. Because of the varying mechanisms of actions associated with colorimetric, fluorometric, and other known detection systems and techniques, it is not always necessary or useful for the dye reagent formulation erodibly released from the polymer carrier within the polymeric reaction matrix to react directly with the analyte of interest. Rather, the dye reagent formulation once released may irreversibly react with a variety of other molecules which have been described and termed absorbers, proto-absorbers, and/or absorption complexes within U.S. Pat. No. 4,822,746, the text of which is expressly incorporated by reference herein. Accordingly, the reagent formulation may react with either the true analyte or with another molecule of interest which is present and indicative of the analyte within a test fluid, preferably a liquid aqueous solution.

II. The Essential Component Parts of the Fiber Optic Sensor

There are only three essential components comprising the improved fiber optic sensor. These are: an optical fiber strand having a proximal end, a distal end, and a strand length; a polymeric reaction matrix immobilized substantially at and around the distal end of the optical fiber strand; and at least one and preferably a plurality of controlled release polymer carriers within the thickness and body of the polymeric reaction matrix. Each component part will be described individually.

Optical Fiber Strands

The use of optical fiber strands for detection purposes and within fiber optic sensors is well known in this art. Such glass fibers are described in: U.S. Pat. No. 4,577,109; and in Milanovich et al., "Novel Optical Fiber Techniques For Medical Application," published in *Proceedings Of The SPIE 28th Annual International Technical Symposium On Optics And Electroptics*, volume 494 (1984). In general, light from a light energy source is used to illuminate the proximal end of the optical fiber strand, the light having a predetermined wavelength. The light energy is carried by the optic fiber strand along its length and exits from the distal end for illumination with radiant light energy. The composition of the fiber strand is preferably glass but may be comprised of polymeric materials as well. Accordingly, any and all compositions presently known or to be employed in the future as an optic fiber strand may be used to make the present invention without limitation.

The Polymer Carrier

The discrete polymer carriers used in the present invention comprise a controlled release polymer and a releasable reagent formulation able to react irreversibly or reversibly with a prechosen molecule, entity, or analyte of interest. Thus, the controlled release polymer and the reagent formulation forming each polymer carrier each serves a separate and distinct purpose and function. Clearly, the purpose of the reagent formulation is to react with the analyte of interest and form a reaction adduct product which is colored and thus optically detectable. In contrast, the role of the controlled release polymer is to provide a controlled release over time of the chosen reagent formulation from the formed carrier such that the analyte of interest in each test fluid or sample in sequence is optically detected seriatim.

Controlled release polymers, their properties and characteristics, their structures and formulations, and their modes of action have been an area of intensive investigations in unrelated technical fields, particularly as a form of drug administration and in delivery systems of drugs in-vivo.. Controlled release polymers, as a class of compositions, are able to release a ligand of choice over a large range of disparate time periods and at greatly varying rates of release; and act almost independently of markedly different environmental conditions in-vitro and in-vivo. Merely representative of the information, knowledge, and applications conventionally known for controlled release polymers are the following publications, each of which is expressly incorporated by reference herein: Langer, R., *Science* 249:1527–1533 (1990) and the references cited therein; Benita et al., *J. Pharm.* 73:1721–1724 (1984) and the references cited therein; Watts et al., *J. Controlled Release* 16:311–318 (1991) and the references cited therein; and U.S. Pat. Nos. 4,897,268; 4,897,267; 4,897,268; and the references cited therein.

It is generally recognized and accepted by ordinarily skilled practitioners in this art that controlled release polymers as a class function and achieve their purpose using a variety of different mechanisms of action including diffusion, chemical reaction, and solvent activation. Two types of diffusion controlled release of a chosen ligand are known: reservoir systems and matrix systems. Alternatively, release by chemical control is accomplished typically either by polymer degradation or chemical cleavage of the chosen ligand from a polymer. Lastly, solvent activation involves either swelling of the polymer or osmotic effects causing release of the chosen ligand [see Langer, R., *Science* 249:1527–1533 (1990) at page 1529].

The present invention intends and expects that the entire membership comprising the class of controlled release polymers, individually and collectively, be available for use in the present invention regardless of the particular formulation and structure, format requirements, or mechanism of action by which a chosen ligand becomes controllably released. Thus, all the conventionally known controlled release polymers are believed useful in preparing discrete polymer carriers; and all of these will provide a controlled release of a chosen reagent formulation—albeit at varying rates of release, over disparate time intervals, and using alternative mechanisms of action to achieve release of the reagent formulation from the discrete carrier.

In its simplest mode, the user will employ only one particular controlled release polymer in combination with only one specific reagent formulation when constructing the discrete polymer carriers for use in a single type of sensor. This mode of sensor construction will then provide for a controlled release of a single reagent formulation at a single sustained rate of release for a single time duration, with only minor, insignificant differences between individual embodiments of the same type of construction.

The present invention, however, also expects and intends that a more complex kind of sensor be constructed utilizing multiple and different controlled release polymers in combination with multiple and different reagent formulations to form a range of divergent and heterogeneous discrete polymer carriers, each of which has its own singular controlled release polymer and its own individual reagent formulation. In this complex mode of construction, there exists a range of differently formulated polymer carriers which may be varied individually in the kinds and assortment of reagent formulations released, in the rates at which each of the different reagent formulations are released, and the different time intervals over each of which the various individual reagent formulations are released Thus, within a single sensor, the use of a mixture of different discrete polymer carriers can provide a range of slow, intermediate, or fast rates of controlled release for a single reagent formulation or a prechosen set of different reagent formulations Similarly, using a mixture of different discrete polymer carriers can provide a divergent range of differing time durations for controlled release of one or more reagent formulations - such timing being continuous, intermittent at preset intervals, or irregular as needed or desired by the user or the specific application. All of these factors and variables are deemed to be within the scope of the present invention.

A most favored type of controlled release polymer for use in forming the discrete polymer carriers is he fluid-erodible polymer which provides a continuous and sustained release of a prechosen reagent formulation. Many continuous release polymers which are erodible by liquids, preferably aqueous solutions, for the controlled release of reagent formulations useful as ligands in optical determinations are commonly known. A representative listing of fluid-erodible, non-erodible, and other controlled release polymers is provided by Table 1; and a representative listing of reagent formulations of diverse composition and properties is provided by Table 2.

TABLE 1

| I. Erodible Controlled Release Polymer |
|---|
| Polyanhydrides (and copolymers and homopolymers) |
| poylsebacic acid |
| poly(p-carboxyphenoxy)propane |
| poly(p-carboxyphenoxy)hexane |
| poly-isophthalic acid |
| Vinyl Polymers (and copolymers and homopolymers) |
| ethylene vinyl acetate copolymer |
| polyvinylpyrrolidone |
| polyvinyl alcohol |
| Polyacrylamides |
| poly-2-hydroxyethyl methacrylate |
| Polyglycolic Acids |
| polyglycolide |
| polylactide |
| pollyglycolide/lactide copolymer |
| polyhydroxybutyrate |
| polyhydroxy valerate |
| polycaprolactones |
| II. Non-erodible Controlled Release Polymers |
| Hydrogels |
| polyacrylamide |
| polyvinyl alcohol |
| poly(2-hydroxyethyl methacrylate) |
| poly-N-(2-hydroxypropyl methacrylamide) |
| poly vinylpyrrolidone |
| polymethyl methacrylate (as adjuvants) |
| Hydrophobic polymers |
| ethylene vinyl acetate copolymer |
| silicone elastomers |

TABLE 1-continued microporous polypropylene
cross-linked (meth)acrylates

III. Biodegradable Controlled Release Polymers polyactic acid (polylactide)
polyglycolic acid (polyglycolide)
poly (lactic acid-co-glycolic acid)
poly (ε-carprolactone): polyvalerolactone
poly (hydroxybutyric acid-co-hydroxyvaleric acid)
poly orthoesters
poly alkylcyanoacrylates
synthetic polypeptides
cross-linked polypeptides and proteins
natural polymers: albumin, gleatin, starch
polyanydrides:
monomers for: sebacic acid
bis(p-carboxy-phenoxy)-propane
dodecandedioic acid

IV. pH Sensitive Controlled Release Polymers cellulose acetate trimelltiate
hydroxypropyl methyl cellulose phthalate
cellulose acetate
cellulose acetate propioinate
cellulose triacetate
copolymers of methacrylic acid and methacrylic acid methyl ester
(Eudragit L100$^R$)

TABLE 2
REAGENT FORMULATIONS

Indicator Compounds and Dyes
absorbers
protoabsorbers
absorption complexes
chromophoric compounds
chromogenic compounds
fluorophoric compounds
fluorogenic compounds

Labelled Immunological and Immunochemical Compositions
labelled antigens
labelled haptens
labelled antibodies and antibody fragments

Enzyme Systems Components and Compositions
enzymes and zymogens
enzyme substrates and substrate analogues
cofactors The most desirable fluid-erodible materials for use as controlled release polymers are ethylene-vinyl acetate (EVA) copolymers and lactide glycolide (LG) polymers. EVA operates by swelling in the presence of water which forms pores through which reagent is released. LG polymers undergo surface hydrolysis which erodes the polymer and releases trapped reagent The LG polymers possess the advantage that release rates can be tailored simply by using different initial monomer ratios. A summary of the various materials is shown in Table 3.

TABLE 3

| Polymer | Mechanism |
| --- | --- |
| Ethylene-vinyl acetate | Swelling - pore formation |
| Glycolide | Hydrolysis - erosion (rapid) |
| Lactide | Hydrolysis - erosion (long) |
| Glycolide/lactide | Hydrolysis - erosion (variable) |

Both of these preferred materials are soluble in organic solvents including solvent mixtures such as methylene chloride and methanol Aqueous solutions cannot be used without causing swelling (EVA) or hydrolysis (LG). Consequently, water-soluble reagents typically are incorporated into these polymers in particulate form. These particles can compromise the performance of the controlled release polymers by causing concentration pulses; this event, however, does not preclude their use in the present invention.

It is most desirable that organic soluble reagents that can be incorporated homogeneously into the two controlled release polymer systems be employed Fluorescent dyes such as fluorescein and rhodamine are soluble in organic solvents and can be incorporated into EVA and LG polymer systems. Dye loadings will typically range from 1-50%. Polymer-dye solutions will be cast either in block form and cut to the desired size or will be formed into various shapes (e.g., cubes hemispheres) using molds.

If small polymer carrier particles are needed, the polymers are preferably crushed and sieved to provide ranges of sized particles Another approach to preparing small particles is to atomize the dye-polymer solution into a vacuum chamber. The small droplets will form spheres and solvent should evaporate quickly providing small spheres of controlled release polymers. Alternatively, any other conventionally known physical format and construction including spheres, capsules, microparticles, and the like may be employed.

Fluid erodible controlled polymer carriers are also preferred for the sustained release of macromolecules such as polypeptide hormones, polysaccharides, antigens, antibodies, and enzymes. These have been described in the scientific literature [Chasin et al., *BioPharm. Mfg.* 2:33-41 (1988); Langer, R., *Chemtech.* (12):98-105 (1982); Langer, R., *Meth. Enzymol.* 73:57-73 (1981); Rhine et al., *J. Pharm. Sci.* 69:265-270 (1980); Langer, R. and J. Folkman, *Nature* 263:797-799 (1976). All of these references are expressly incorporated by reference herein.

Similarly, the releasable reagent formulations may be selected from a wide and diverse range of compositions and properties. The releasable ligands include known indicator or dye compounds useful within ultraviolet, visible, fluorescent, phosphorescent, and other well defined optical systems and methods. Accordingly, these include the known colorimetric compositions known as absorbers, protoabsorbers, absorption complexes, chromophoric and chromogenic compositions, and fluorophoric and fluorogenic compounds—all of which are known and described in the relevant scientific and industrial literature.

In addition, the releasable reagent formulation may also have other attributes and capabilities such as specific binding properties. Accordingly, such reagent formulations include all the conventionally known labelled immunological compositions including labelled antigens, haptens, and other antibody or cellular immunological and/or immunochemical components. Moreover, there are many applications where the components of known enzyme systems are valuable for use as the releasable reagent formulations. Such instances include specific enzymes of various and divergent specific activity, their specific enzyme substrates and/or substrate analogues, and the requisite cofactors necessary for the enzyme reaction to proceed. Furthermore, recognizing that the listing of Table 2 above is merely representational and illustrative of the range and variety of reagent formulations which are able to be immobilized within a controlled release polymer, any and all other compositions, ligands, and chemical molecules or moieties which have value and utility as an irreversible or reversible binding indicator by which to make an optical determination—in quantitative or qualitative terms using any known mechanism of action or technique—are all deemed to be within the scope of the present invention.

The Polymeric Reaction Matrix

The present invention recognizes and relies upon the fact that many controlled release polymers (such as EVA) tend to release dye reagent quickly and often exhaust their dye content within several days or weeks due to the high surface/volume ratio of microparticles or the small amount of erodible polymer employed. To mitigate this relatively rapid release rate, the present invention incorporates these controlled release polymers as preformed carriers in a variety of hydrophilic polymeric reaction matrices or gels such as polyacrylamide and polyHEMA. By suspending these polymer carriers in gel matrices of varying physical properties, diffusion of liquids will be slowed and lead to longer lasting sensors. These gel matrix materials will be prepared by adding the controlled release polymer particles to secondary polymerizing reaction mixtures when the reaction gel viscosity is appropriate An additional advantage of this configuration is that in many instances the supporting or surrounding gel reaction matrix acts to smooth out any extreme pulses or release irregularities in concentration of reagent formulation being released. In other cases, the gel matrix may serve only as a holding vehicle and chamber in which to position and immobilize the discrete controlled release polymer carriers or to provide a diffusion barrier for the reaction adduct product being formed by the released agent formulation and the analyte of interest. Even in these instances, the sensor provides the desirable advantages and major benefits of faster response times, smaller sensor sizes, and increased ease of manufacture in comparison to conventionally known constructions.

A preferred, non-exhaustive but representative listing of monomers, copolymers, and homopolymers suitable for use as gels in the prepared porous and fluid permeable polymeric reaction matrix to be immobilized at and/or around the distal end of an optical fiber strand is given by Table 4.

TABLE 4

| POLYMERIC REACTION MATRIX MATERIALS |
| --- |
| Polyacrylamide - methylene bisacrylamide copolymer |
| Polyacrylamide |
| Polymethyl acrylamide |
| Polyhydroxyethyl acrylamide |
| polyvinyl alcohol |
| polyurethanes |

III. Experiments and Empirical Data

Apparatus

Two different instrumentation systems were used in the two experimental approaches described below. The first system [described previously in Munkholm et al., *Anal. Chem.* 58:1427–1430 (1986)] employs a 488 nm argon-ion laser as the excitation source. Light is conducted through a series of lenses and filters into an optical fiber strand (Corning Core Guide glass NA (numerical aperture) =0.28). The fluorescence is conducted back through the same fiber strand and reflected by a dichroic mirror to a photomultiplier tube. The intensity of the fluorescence is measured as a function of emission wavelength using a photon-counting detection system (Pacific Instruments, Model 126).

The second variable wavelength optical system is schematically shown in FIG. 2. This system can be used to measure fluorescence intensity at different excitation wavelengths at a fixed emission wavelength and consists of four basic components: a variable wavelength light source for excitation; an optical system for conducting light into the sensor and to the detector; an emission detection system; and computer control and data acquisition system.

The excitation light source consists of a 75 watt high pressure Xenon arc lamp (Osram Company) which gives a continuous spectrum from 190 nm to 750 nm and a Spex 1680 0.22 m double monochromater for selecting any specified wavelength light. The use of a double monochromater ensures low stray light levels in the excitation. The optical system consists of lenses and mirrors that focus the excitation light onto the fiber, retrieve the emission light from the fiber and focus it onto the entrance slit of the emission detection system. The emission detection system is comprised of a second Spex 1680 0.22 m double monochromater with a 300 lines/mm grating and a RCA 31034A-02 photomultiplier tube. The detected signal is then processed b a photometer. Finally, a PC-AT with an AD (analog to digital) and DA (digital to analog) board is used to acquire and display the data, and to control the movements of the stepping motors in the excitation and emission spectrometers.

To demonstrate the utility and efficacy of the improved fiber optic sensor comprising the present invention, a variety of experiments and empirical data will be described hereinafter. It will be expressly understood, however, that these experiments and empirical results are merely descriptive of the various embodiments comprising the present invention as a whole; and serve merely to illustrate some of those situations and applications in which the present invention may be usefully employed. None of the experimental models, empirical data, or conclusions are deemed to be restrictive of the present invention in any form or use; to the contrary, it will be recognized and appreciated that these experiments merely demonstrate the variety of applications and the range of effective parameters one may expect to be in effect when employing the present invention.

EXAMPLE 1

A First Sensor Embodiment

Polymeric Carrier Preparation

Ethylene-vinyl acetate copolymer (EVA) pellets were first washed at least three times in distilled water with constant stirring. The EVA pellets were then extracted in a Soxhlet extractor with high quality acetone for at least three days. The EVA pellets were then quickly removed from the paper thimble at the end of the extraction while the acetone was still hot. Finally, the EVA pellets were dried in a dessicator under house vacuum for at least a week. Drying was complete when all acetone had evaporated.

The EVA copolymer was dissolved in methylene chloride to give a 10% w/v solution. A weighed amount of 8-hydroxypyrene-1,3,6-rrisulfonic acid (HPTS) was added to 15 mL of the polymer solution in a glass vial to give a dye loading of 33%. In the case of the HPTS and sulforhodamine 640 (SR640) mixture, a one to one ratio was employed, and the total loading in the polymer was 33%. Each prepared mixture was vortexed to yield a uniform suspension. After vortexing, the prepared mixture was poured quickly into the center of a glass mold (5×5×2 cm), which had been cooled previously in a freezer for 20 minutes. The glass mold was covered and remained in the freezer until the prepared mixture froze (about 30 minutes). The frozen particle slab was then easily pried loose with a cold spatula; transferred onto a wire screen; and kept in the freezer for two days. The frozen particle slab was dried for an additional two days at room temperature in a dessicator under house vacuum. The dye-containing EVA particles were prepared from EVA slabby sieving the polymer slab on a molecular sieve (obtained from Dual Manufacturing Co., Chicago, IL) for sizes ranging from 75–250 microns.

Sensor Construction

To construct the sensor shown in FIG. 1, the optical fiber distal tip was first cleaned with concentrated sulfuric acid and rinsed with distilled water. The distal end was then silanized with γ-methacryloxypropyltrimethoxysilane. The silanized fiber was inserted into a 4-cm long capillary tube (leaving 0.5–1 cm length covering over the fiber tip); and was fixed in position by wrapping Parafilm around the fiber coating and the end of the capillary tube. The fiber with the capillary tube on it was inverted and photopolymerized with 1:1 equivalent of acrylamide (10 g in 20 mL of phosphate buffer, pH 6.6) and BIS (1.2 g in 100 mL of propanol) using 2 equivalents of benzoin ethyl ether (100 mg in 1 mL of propanol) as a radical initiator under UV light for 5 minutes. About 2 mg of HPTS-containing EVA particles was added during the photopolymerization. Before photopolymerization, the mixture of monomers and the radical initiator should be degassed with $N_2$ or Ar to remove dissolved $O_2$.

Release Kinetics of EVA Particles in the Sensor

Figure 3:
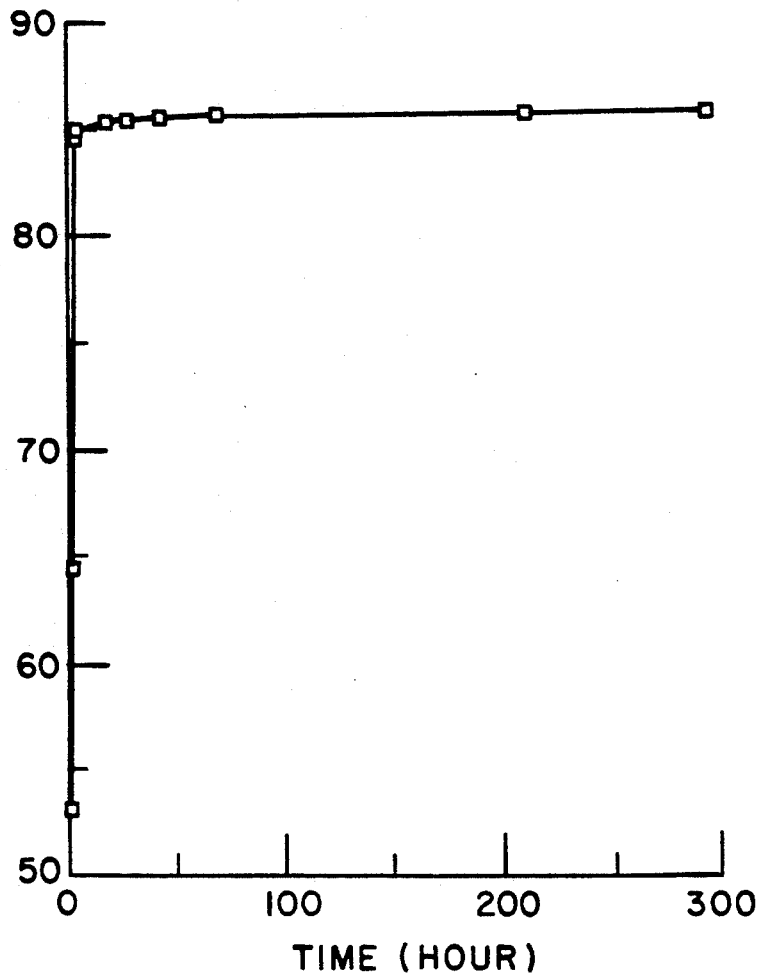
FIG. 3 is a graph illustrating the release kinetics of HPTS in EVA particles.

The release kinetics of 30% HPTS in EVA particles is shown in FIG. 3. It is observed that more than 80% of HPTS is released from the particles at the first three-hour period. This is due to a large amount of surface area of polymer carrier particles that facilitated fast release of HPTS. After that period, the rate of release slowed down and continued for about 12 days.

EXAMPLE 2

An Embodiment With Solid Coatings as Polymer Carriers

Sensor's Configuration

Figure 4:
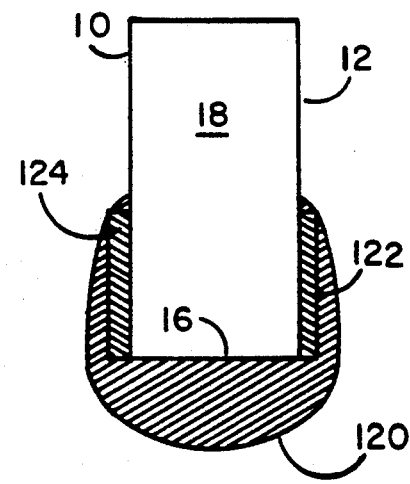
FIG. 4 is a cross-sectional view of a second embodiment of the fiber optic sensor.

A second design using a coating method was developed and its configuration is shown in FIG. 4. The side of the distal end of the optical fiber was first dip coated with HPTS-containing EVA and the distal tip of the fiber was later enclosed by a layer of porous polymeric reaction matrix which serves as a reaction chamber and allows the reagent and analyte of diffuse freely.

Experimental Section

Approximately 3 cm length of buffer and cladding at the fiber tip was first removed and the exposed part was dip-coated 10 times in a 10% ethylene vinyl acetate copolymer (DuPont Corp.) solution ($CH_2Cl_2$ as a solvent) with HPTS loading of 33% or 67%.

After solvent had evaporated, the distal fiber tip was cleaved to ensure a clean and smooth surface and the polymer carrier coating was kept about 0.5–1 cm long. Then the fiber was inverted and a drop of γ-methacryloxypropyltrimethoxysilane was dripped on the distal tip and allowed to react with the fiber surface for 30 minutes. The silanizing reagent was added several times. Finally, the fiber tip was photopolymerized with acrylamide and BIS using the previous procedure. The side of the distal tip was photopolymerized five times by repeatedly dipping the fiber in the monomer mixture and exposing it to the UV light.

Response Time of the Sensor

The same mechanism is operative for the sensor shown in FIG. 4 as for the sensor of FIG. 1. Analyte in the sample solution diffuses into the porous polymeric reaction matrix 120 where it reacts with the indicator dye reagent formulation 124 18 released from the EVA polymer carrier coating 122 on the side of the fiber tip.

Figure 5:
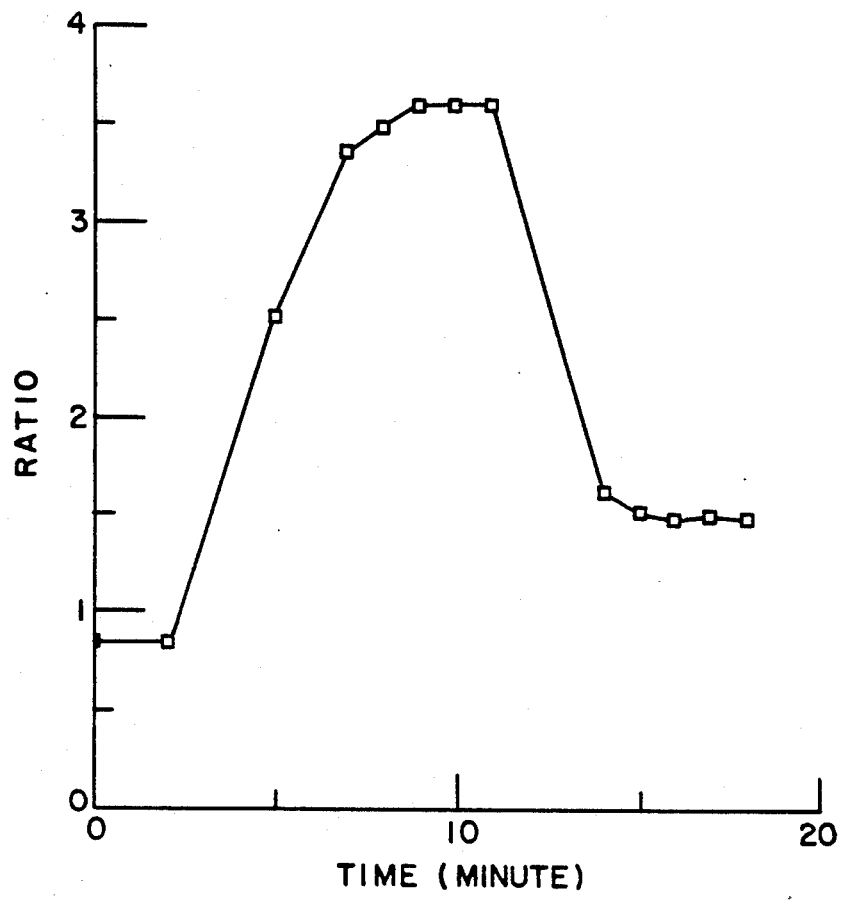
FIG. 5 is a graph illustrating the response time for the second embodiment of FIG. 4.
Figure 6:
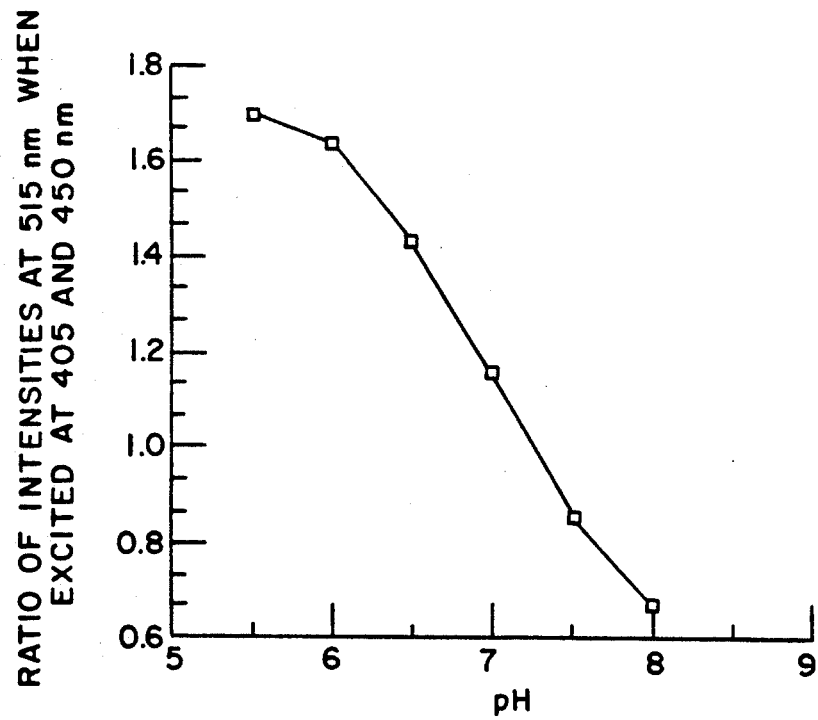
FIG. 6 is a graph illustrating the pH response curve for the second embodiment of FIG. 4.

The response time of this sensor embodiment is governed primarily by the diffusion of analyte in the test fluid through the porous polymeric reaction matrix. Since the size of the reaction matrix or the sensing region is small, the response time per pH unit change was about 4–5 minutes under non-stirred conditions and 1–2 minutes with stirring of the sample solution Some results are demonstrated in FIG. 5 and summarized in Table 5 below.

TABLE 5

| RESPONSE TIME OF THE COATING SENSOR (min/pH) ||
|---|---|
| Non-stirring | Stirring |
| 4–5 minutes | 1–2 minutes |

Longevity and Response Curve

Since the longevity of this second sensor depends on the amount of EVA polymer carrier, a sensor with EVA coated on its wall revealed a short lifetime because only a thin layer of polymer was applied as a coating. Thus, only a lifetime of one day was found. The ratio versus pH curve for this sensor is presented in FIG. 5.

The present invention is not to be restricted in form nor limited in scope except by the claims appended hereto.

What I claim is:

1. A fiber optic sensor for performing optical determinations of a plurality of test fluids believed to contain an analyte of interest, said fiber optic sensor comprising:
    a optical fiber strand able to convey light energy of a determinable wavelength, said optical fiber strand having a proximal end, a distal end, and a strand length;
    a discrete, porous polymeric reaction matrix immobilized at the distal end of said optical fiber strand, said analyte of interest to be detected being able to permeate and react within said polymeric reaction matrix; and
    at least one preformed controlled release polymer carrier contained within said immobilized porous polymeric reaction matrix, each of said preformed controlled release polymer carrier comprising at least one controlled release polymer material and at least one reagent formation controllably releasable from said polymer material in mobile form for reaction with such analyte of interest as is present within said polymeric reaction matrix, the reaction between said analyte of interest and said released reagent formulation forming a diffusible and optically detectable product within said polymeric reaction matrix.

2. The fiber optic sensor as recited in claim 1 wherein said reagent formulation is selected from the group consisting of indicator compounds and dyes.

3. The fiber optic sensor as recited in claim 1 wherein said reagent formulation is selected from the group consisting of labelled antigens, labelled haptens and labelled antibodies and antibody fragments.

4. The fiber optic sensor as recited in claim 1 wherein said reagent formulation is selected from the group consisting of enzymes and zymogens, enzyme substrates and substrate analogues, and cofactors.

5. The fiber optic sensor as recited in claim 1 wherein said controlled release polymer is a polyanhydride.

6. The fiber optic sensor as recited in claim 1 wherein said controlled release polymer is a vinyl polymer.

7. The fiber optic sensor as recited in claim 1 wherein said polymeric reaction matrix is a polyacrylamide.

8. The fiber optic sensor as recited in claim 1 wherein said controlled release polymer carrier is fluid erodible.

9. A fiber optic sensing apparatus for performing optical determinations of a plurality of test fluids believed to contain an analyte of interest, said sensing apparatus comprising:
a fiber optic sensor comprised of:
a optical fiber strand able to convey light energy of a determinable wavelength, said optical fiber strand having a proximal end, a distal end, and a strand length,
a discrete, porous polymeric reaction matrix immobilized at the distal end of said optical fiber strand, said analyte of interest to be detected being able to permeate and react within said polymeric reaction matrix, and
at least one preformed, controlled release polymer carrier contained within said immobilized porous polymeric reaction matrix, each of said preformed controlled release polymer carrier comprising at least one controlled release polymer material and at least one reagent formulation controllably releasable from said polymer material in mobile form for reaction with such analyte of interest as is present within said polymeric reaction matrix, the reaction between said analyte of interest and said released reagent formulation forming a diffusible and optically detectable product within said polymeric reaction matrix;
a source of light energy of determinable wavelength;
means for conveying light energy from said source to said proximal end of said optical fiber strand;
means for detecting light energy; and
means for conveying light energy from said optical fiber strand to said detecting means.

10. The fiber optic sensing apparatus as recited in claim 9 further comprising a computer control and data acquisition system.

11. The fiber optic sensing apparatus as recited in claim 9 wherein said light energy is in the ultraviolet light range.

12. The fiber optic sensing apparatus as recited in claim 9 wherein said light energy is in the visible light range.

13. A method for performing optical detections of a plurality of test fluids believed to contain an analyte of interest, said method comprising the steps of:
providing a fiber optic sensor comprised of:
a optical fiber strand able to convey light energy of a determinable wavelength, said optical fiber strand having a proximal end, a distal end, and a strand length,
a discrete, porous polymeric reaction matrix immobilized at the distal end of said optical fiber strand, said analyte of interest to be detected being able to permeate and react within said polymeric reaction matrix, and
at least one preformed, controlled release polymer carrier contained within said immobilized porous polymeric reaction matrix, each of said preformed controlled release polymer carrier comprising at least one controlled release polymer material and at least one reagent formulation controllably releasable from said polymer material in mobile form for reaction with such analyte of interest as is present within said polymeric reaction matrix, the reaction between said analyte of interest and said release reagent formulation forming a diffusible and optically detectable product within said polymeric reaction matrix;
introducing a test fluid to the distal end of said fiber optical sensor whereby at least a portion of such analyte of interest as is present in said fluid permeates said polymeric reaction matrix and reacts with such reagent formulation as has been controllably release into said polymeric reaction matrix to form a diffusible and optically detectable product;
conveying light energy of determinable wavelength to said proximal end of said optical fiber strand; and
detecting light energy conveyed by said optical fiber strand from said polymeric reaction matrix after formation of said diffusible and optically detectable reaction product by said release reagent formulation and the analyte of interest, said detected light energy being a measure of the analyte of interest in the test fluid.

* * * * *